United States Patent [19]

Regnault

[11] Patent Number: 4,568,947
[45] Date of Patent: Feb. 4, 1986

[54] CONDUCTIVE FLUID TURBULENCE DETECTION SYSTEM

[75] Inventor: Luc Regnault, Bourg les Valence, France

[73] Assignee: Imaje S.A., Bourg les Valence, France

[21] Appl. No.: 591,478

[22] Filed: Mar. 20, 1984

[30] Foreign Application Priority Data

Mar. 25, 1983 [FR] France .................. 83 05297

[51] Int. Cl.[4] .................. G01D 15/18; G01F 1/56; G08B 21/00
[52] U.S. Cl. .................. 346/75; 346/140 R; 73/861.08; 340/606; 340/611
[58] Field of Search .................. 346/75, 140 R; 73/861.08; 340/603, 606, 611

[56] References Cited

U.S. PATENT DOCUMENTS

| | | | |
|---|---|---|---|
| 4,183,029 | 1/1980 | Isayama et al. | 346/140 R |
| 4,346,388 | 8/1982 | Wiley | 346/75 |
| 4,364,055 | 12/1982 | Aiba | 346/1.7 |

Primary Examiner—E. A. Goldberg
Assistant Examiner—Gerald E. Preston
Attorney, Agent, or Firm—Roland Plottel

[57] ABSTRACT

A safety device for the conductive-fluid circulation system of an ink-jet printer consists of a sensor and an associated electronic circuit inserted between an ink-drop recovery trough and a recirculating pump. The level of turbulence of the fluid flow within a pipe segment of insulating material located between two conductive pipe segments is determined by the sensor by measuring the variation in conductivity in relation to variations in cross-sectional area of fluid within the insulating pipe segment and by delivering a control logic signal.

8 Claims, 3 Drawing Figures

CONDUCTIVE FLUID TURBULENCE DETECTION SYSTEM

BACKGROUND OF THE INVENTION

1. Field of the Invention

The invention relates to a safety device used in systems for circulating a conductive fluid, especially ink-jet recovery circuits in continuous ink-jet printers.

2. Description of the Prior Art

A frequent problem lies in the need to check whether a flow of conductive fluid split-up in the form of drops within a pipe of small diameter is taking place under acceptable conditions which are conducive to good operation of the installation or on the contrary whether any irregularities have developed and justify remedial measures.

A problem of this nature arises particularly in the field of ink-jet printers. In fact, among the different ink-jet printing techniques, a certain number are based on the use of a continuous stream of ink drops from which part of the stream is withdrawn for the purpose of printing characters. The other drops are recycled in a special circuit known as a recirculation circuit. Now a key function of this device is the so-called "dump" zone for collecting the unused stream of drops to be recycled. Taking into account the nature of the inks employed which are capable by definition of very rapid drying and also taking into account the small cross-sectional area of the collecting element, blockage may eventually occur. Another potential danger lies in the possibility of failure of the pumping means. In all cases there is a risk of overflow of ink which would have a damaging effect on the installation. In order to avoid the consequences which would result from an operational fault condition of this type, it is a desirable objective to provide means for detecting such a fault condition in order to take the necessary steps without delay. And this is precisely the aim of the present invention.

SUMMARY OF THE INVENTION

In accordance with the invention, a sensor is adapted to cooperate with an electronic circuit in order to detect the appearance of a fault condition in the circulation of a conductive fluid within a pipe of small diameter. The sensor accordingly delivers a signal which can serve to initate a sequence for ensuring correct operation while meeting safety requirements, for example by completely stopping the machine.

The invention is more specifically concerned with a safety device applied to a system for circulating a conductive fluid of the type comprising a pipe for delivering the fluid to a pump. The distinctive feature of the invention lies in the fact that it permits measurement of the level of turbulence within the pipe by measuring variations in conductivity of the fluid arising from variations in cross-sectional area of said fluid within a pipe segment of predetermined length L and formed of insulating material.

BRIEF DESCRIPTION OF THE DRAWINGS

Other features of the invention will be more apparent upon consideration of the following description and accompanying drawings, wherein.

DETAILED DESCRIPTION OF THE INVENTION

For the sake of enhanced clarity, the same elements are designated by the same references in all the figures.

As stated earlier, the non-limitative example chosen for the purpose of illustrating the invention relates to the circuit for recirculating the ink stream not employed for printing, in an ink-jet printer. The recovered ink stream is collected by a pipe which cooperates with a pumping means as will be explained hereinafter and returns the ink to the supply tank for subsequent reuse. The pipe under consideration has a diameter of the order of one millimeter and receives a stream of spaced drops having a diameter which is from five to ten times smaller.

If the flow were perfect and non-turbulent, air would circulate at the center of the tube and the ink entrained by friction would circulate at the periphery. But the action of gravity, friction forces, the substantial difference in viscosity between air and ink as well as other parameters in fact produce turbulent flow.

The present Applicant has found by experiment that a characteristic flow pattern corresponds to normal recirculation. In fact, the cross-sectional area of ink as it flows within the pipe is very irregular. For a given length of piping, there is therefore a variation in conductivity, the frequency of which indicates the quality of flow of fluid at this level. Experimentally, the present Applicant has found, for example, that with a tube 2 mm in diameter and a vacuum of approximately 200 millibars, the variation in conductivity takes place with a spectrum having a large number of components which vary between 40 and 100 Hz.

Figure 1:
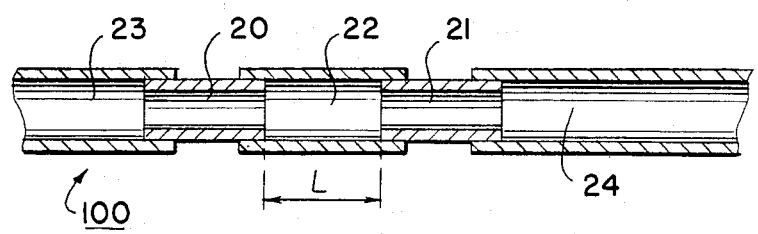
FIG. 1 is a schematic representation of a sensor which is intended to cooperate with an electronic circuit in order to constitute a safety device in accordance with the invention.

In accordance with the invention, a sensor 100 as illustrated schematically in FIG. 1 is interposed in the recirculation pipe. This sensor consists of a pipe segment made up of two conductive elements 20 and 21 which delimit an insulating element 22 having a length L which will hereinafter be designated as an insulating segment. The conductive elements are connected to the remainder of the insulating pipe 23 and 24 in a conventional manner. The combination of the two conductive elements 20 and 21 and of the insulating segment 22 constitutes a sensor 100 which is adapted to cooperate with an electronic circuit 101 shown in FIG. 2. The design function of said sensor as contemplated by the invention is to measure the variations in conductivity of the fluid and the frequency of such variations, the measurement being performed at the level of said insulating segment 22. A comparison is then made with a reference signal which makes it possible to obtain an output logical signal having a level 0 to 1 which can be employed as the control signal of a safety device.

Figure 2:
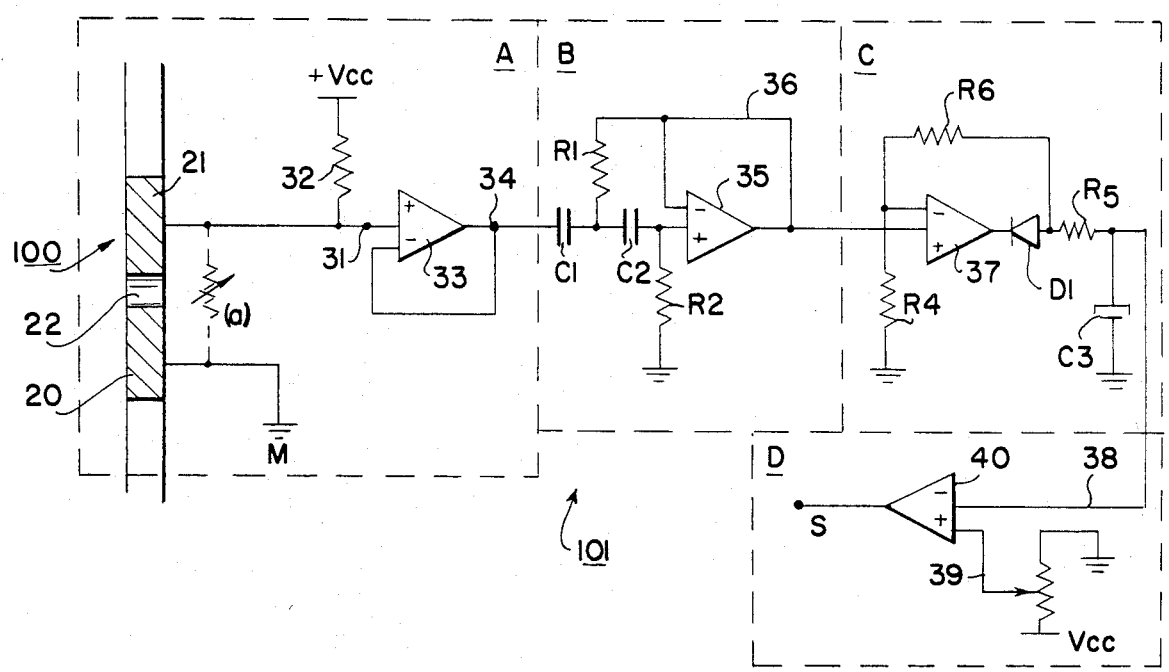
FIG. 2 shows one example of construction of an electronic circuit of this type.

One example of construction of an electronic circuit 101 of this type is illustrated schematically in FIG. 2. This circuit essentially consists of four elements or subassemblies A, B, C, D, the functions of which are described hereunder.

These subassemblies are essentially as follows:

A: a generator for producing voltage which is a function of the variations in conductivity of the fluid segment contained in the insulating segment 22 of the sensor 100;
B: a bandpass filter for delivering a filtered signal;
C: a voltage-amplifying peak detector;
D: a comparator.

The first subassembly A comprises the sensor described earlier and the variation in conductivity which occurs at the level of the insulating segment 22 is indicated by the conventional representation of a variable resistance (a). The conductive element 200 is connected to ground M. This variation in conductivity (a) is converted to a variation in voltage by means of the load resistor 32. An amplifier 33 produces a substantial drop in the impedance applied to its input 31. The signal 34 at the output of the amplifier 33 has a voltage equal in value to that of the signal 31 and is filtered in subassembly B of the circuit 101 by means of a bandpass filter constituted by the resistors R1 and R2 and the capacitors C1 and C2, said bandpass filter being in turn followed by an amplifier 35. The resultant filtered signal 36 is applied to the input of subassembly C of the circuit 101 which performs the function of peak detector and voltage amplifier. This circuit element or subassembly C comprises three resistors R4, R5, R6, a capacitor C3, a diode D1 and an amplifier 37. Said subassembly generates a direct-current voltage 38 which is a function of the peak values of the signal 36 and therefore of the rapid variations in conductivity of the fluid which circulates within the insulating segment 22. Subassembly D is a comparator composed of an operator 40, the function of which is to compare the signal 38 with an adjustable reference signal 39 in order to deliver an output signal S.

When the flow of fluid within the insulating segment 22 is satisfactory, the entire safety device constituted by the combination of sensor 100 and of circuit 101 generates a signal having a logic level "1" at the output S. If the flow is either zero or non-turbulent as a result of low vacuum within the pipe, the output S of the device generates a signal having a logic level "0". This signal S which is representative of the state of turbulence of the fluid can serve as a control signal for a safety device.

Figure 3:
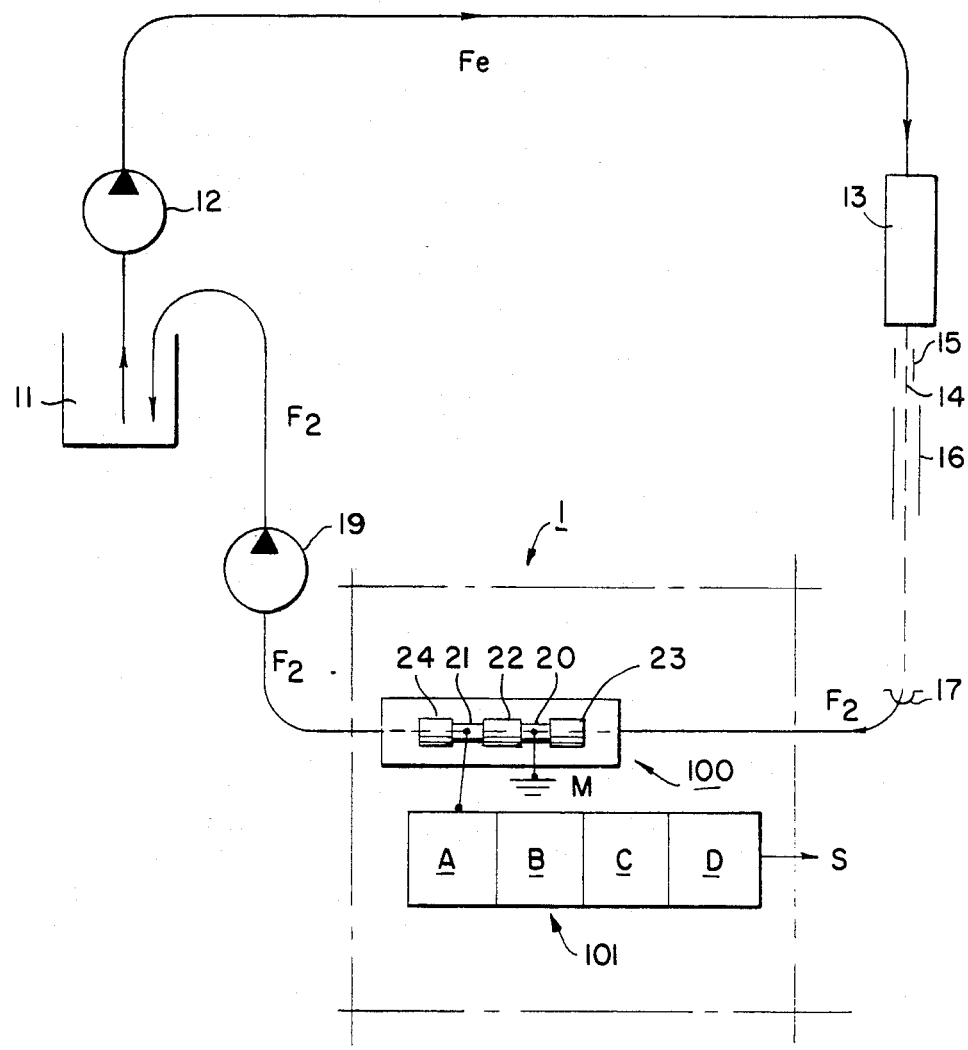
FIG. 3 is a schematic representation of a device for recirculation of the ink stream in a continuous ink-jet printer.

A safety device in accordance with the invention as applied to an ink-jet printer is represented schematically in FIG. 3. A printer of this type essentially comprises an ink reservoir 11 and a first pump 12 for putting this ink under pressure. The ink is then directed via a supply line (fe) to the device 13 for forming the jet 14 consisting of a succession of calibrated ink drops. These drops are charged electrostatically by means of charging electrodes 15 before passing between two deflecting plates 16 in order to be deflected and directed to a substrate to be printed (not shown in the drawings). The unused drops are collected by a recirculation trough 17 and returned via a recirculation pipe (f2) to the ink reservoir 11 by second pumping means such as a recirculating pump 19.

In accordance with the invention, a safety device 1 formed by the combination of a sensor 100 and an associated electronic circuit 101 is interposed in the recirculation circuit (f2) between the collecting trough 17 and the recirculating pump 19. The schematic diagram shows the insulating segment 22 having a length L which is rigidly fixed to the conductive elements 21 and 20 on each side of said segment. The element 20 is connected to ground M and the element 21 is connected to the input of the electronic circuit 101 comprising four circuit subassemblies A, B, C, D, the structure and functions of which have been defined earlier. The ink used for the formation of drops which are intended to be charged electrostatically is conductive by nature. At the level of the recovery pipe (f2) which connects the collecting trough 17 to the pump 19, a turbulent flow must take place in order to ensure correct operation. The level of optimum turbulence is known in the case of each application as a function of the different parameters which characterize the printer such as type of ink, size of drops, dimension of piping, and so on. For example, in the case of a tube 2 mm in diameter and a vacuum of approximately 200 millibars, the variation in conductivity takes place within a spectrum comprising a large number of components ranging from 40 to 100 Hz. As has been stated earlier, the safety device 1 has the function of performing measurements in order to determine whether the level of turbulence satisfies these criteria within the recirculation pipe (f2). Should this be the case, the output signal S is at level 1; otherwise it is at level 0. Arrangements can then be made to overcome this operational fault and to prevent any danger of ink overflow.

In an alternative embodiment of the invention, the first conductive portion of the sensor 100 is constituted by the ink-drop collecting trough 17 itself. This is conducive to a response time of minimum duration between the appearance of a fault condition and activation of safety system circuits.

A safety device of this type serves to protect the integrity of equipment and its environment. Indeed an overflow of unrecovered ink to be recirculated has a damaging effect and must be avoided as far as possible.

What is claimed is:

1. A safety device for determining the condition of flow of a conductive fluid within a conduit of a circulating system, comprising: sensor means interposed within said conduit being in fluid communication therewith so that said fluid will flow through said sensor means, said sensor means including a pipe segment of insulating material, and first and second conductive means coupled on opposite sides of said insulating pipe segment so that said fluid flows through said first conductive means, said insulating pipe segment and said second conductive means; detecting means connected to said sensor producing an electrical signal for measuring variations in conductivity of said fluid therein determined by variations in cross-sectional area of said fluid to thereby determine the level of turbulence of said fluid within said sensor; and indicator means connected with said detecting means for indicating relative level of turbulence of said fluid.

2. The safety device according to claim 1 wherein said detecting means comprises an electronic circuit connected between said first and second conductive means, said electronic circuit including means for measuring said variations of the electrical signal between said first and second conductive means.

3. The safety device according to claim 2 wherein said signal is in the form of a voltage representing a relative condition of conductivity at a point in time as a function of the cross-sectional area of the fluid within said insulating segment of said sensor.

4. The safety device according to claims 2 or 3 wherein said first and second conductive means comprise a conductive pipe segment coupled at one of its ends to said conduit and at its other end to said insulating segment.

5. The safety device according to claim 4 wherein said electronic circuit comprises first, second, third and fourth subassemblies, serially connected, said first subassembly comprising amplifier means for generating said voltage and for reducing the impedance applied to the input of said circuit; said second subassembly comprising bandpass filter means for filtering the signal delivered by said first subassembly; said third subassembly comprising means for delivering a signal having a direct-current component in functional relationship with the signal delivered by said second subassembly; and said fourth subassembly comprising means for comparing the signal delivered by the third subassembly with a variable-reference signal and for delivering an output logic signal having an "0" level or a "1" level representing the level of turbulence of the fluid within said sensor.

6. An ink-jet printer comprising an ink reservoir, a first pressurizing pump, a device for forming a jet of calibrated drops, a set of charging electrodes, and deflecting plates, a recovery trough, a recirculating pump for recirculating ink from said recovery trough to said ink reservoir, a safety device for determining the condition of flow of the ink between said recovery trough and said recirculating pump, said safety device comprising sensor means through which said ink will flow between said recovery trough and said recirculating pump, said sensor means including a pipe segment of insulating material and first and second conductive means coupled on opposite sides of said insulating pipe segment, detecting means connected to said sensor producing an electrical signal for measuring variations in conductivity of said ink to thereby determine the level of turbulence of said fluid within said sensor, and indicator means connected with said detecting means for indicating relative level of turbulence of said ink, said recirculating pump being capable of delivering a signal which can be utilized as a safety device control signal.

7. The ink jet printer, according to claim 6 wherein said first conductive means is formed by said recovery trough made of conductive material, and wherein said second conductive means comprises a conductive pipe segment coupled with said insulating segment so as to be in fluid communication therewith.

8. The ink jet printer, according to claim 6 or 7 wherein the variation in conductivity has a spectrum in which the components vary within the range of 40 to 100 Hz when the recirculation pipe is 2 mm in diameter and a vacuum is produced by the recirculation pump.

* * * * *